United States Patent
Lee et al.

(10) Patent No.: US 9,492,128 B2
(45) Date of Patent: Nov. 15, 2016

(54) X-RAY PHOTOGRAPHY MACHINE WITH SELECTIVELY COUPLED FLANGES FOR PRESSING MEMBER MOVEMENT

(71) Applicant: RAYENCE CO., LTD., Hwaseong (KR)

(72) Inventors: Chang Hwa Lee, Hwaseong (KR); Min Ho Son, Hwaseong (KR)

(73) Assignee: RAYENCE CO., LTD., Hwaseong (KR)

( * ) Notice: Subject to any disclaimer, the term of this patent is extended or adjusted under 35 U.S.C. 154(b) by 0 days.

(21) Appl. No.: 14/650,856

(22) PCT Filed: Dec. 10, 2012

(86) PCT No.: PCT/KR2012/010692
§ 371 (c)(1),
(2) Date: Jun. 9, 2015

(87) PCT Pub. No.: WO2014/092210
PCT Pub. Date: Jun. 19, 2014

(65) Prior Publication Data
US 2015/0320368 A1    Nov. 12, 2015

(51) Int. Cl.
*A61B 6/04*    (2006.01)
*A61B 6/00*    (2006.01)

(52) U.S. Cl.
CPC .............. *A61B 6/0414* (2013.01); *A61B 6/44* (2013.01); *A61B 6/4441* (2013.01); *A61B 6/502* (2013.01); *A61B 6/54* (2013.01)

(58) Field of Classification Search
CPC .......... A61B 6/0414; A61B 6/44; A61B 6/502
See application file for complete search history.

(56) References Cited

U.S. PATENT DOCUMENTS

| 4,599,738 A | * | 7/1986 | Panetta | ................ | A61B 6/0414 |
| | | | | | 378/180 |
| 4,658,409 A | * | 4/1987 | Summ | .................. | A61B 6/0414 |
| | | | | | 378/117 |

(Continued)

FOREIGN PATENT DOCUMENTS

| JP | H05-244748 A | 9/1993 |
| JP | H10-248839 A | 9/1998 |

(Continued)

OTHER PUBLICATIONS

International Search Report for PCT/KR2012/010692 filed on Dec. 10, 2012.

*Primary Examiner* — Brooke Purinton (57) ABSTRACT

Disclosed herein is an X-ray photography machine (300). The X-ray photography machine includes a transfer apparatus (370) which moves a pressing member (360) which presses a target. The transfer apparatus includes a drive source (371), a drive shaft (374) which is rotated by the drive force of the drive source, first and second pulleys (375 *a,b*) which convert rotational force of the drive shaft into force by which the pressing member is moved, and first and second flanges (379 *a,b*) which make the first pulley depend on the rotational force of the drive shaft. In the present invention, because only a single drive shaft is used to move the pressing member, problems such as the occurrence of noise can be minimized.

5 Claims, 8 Drawing Sheets

(56) References Cited

U.S. PATENT DOCUMENTS

| | | | |
|---|---|---|---|
| 5,526,394 A * | 6/1996 | Siczek | A61B 6/4233 378/145 |
| 5,706,327 A * | 1/1998 | Adamkowski | A61B 6/502 378/208 |
| 7,180,978 B2 * | 2/2007 | McKenna | A61B 6/502 378/37 |
| 2003/0058987 A1 | 3/2003 | Rick et al. | |
| 2007/0183566 A1 | 8/2007 | Tsujita et al. | |
| 2012/0020464 A1 * | 1/2012 | Matsuura | A61B 6/0414 378/208 |
| 2012/0136235 A1 * | 5/2012 | Taku | A61B 5/0095 600/407 |
| 2012/0257724 A1 * | 10/2012 | Nakamura | A61B 6/0414 378/189 |
| 2013/0301796 A1 | 11/2013 | Kim | |

FOREIGN PATENT DOCUMENTS

| | | |
|---|---|---|
| JP | H11-076229 A | 3/1999 |
| JP | 2003-126073 A | 5/2003 |
| JP | 2005-000353 A | 1/2005 |
| JP | 2007-229447 A | 9/2007 |
| JP | 2007-330440 A | 12/2007 |
| JP | 2010-110571 A | 5/2010 |
| JP | 4970065 B2 | 7/2012 |
| KR | 10-2009-0112992 A | 10/2009 |
| KR | 10-2012-0087751 A | 8/2012 |

* cited by examiner

X-RAY PHOTOGRAPHY MACHINE WITH SELECTIVELY COUPLED FLANGES FOR PRESSING MEMBER MOVEMENT

TECHNICAL FIELD

The present invention relates to X-ray photography machines and, more particularly, to an X-ray photography machine that uses mammography.

BACKGROUND ART

X-ray photography is used in a variety of medical fields.

A mammography machine is a kind of X-ray photography machine which is used to detect breast cancer, lesions, microcalcification, etc. A representative conventional mammography machine was proposed in Korean Patent Laid-open Publication No. 10-2009-0112992 (entitled: Mammography machine having large-area digital sensor).

To examine the breast of a patient, the breast that is to be examined must be pressed. Thus, mammography machines include a pressing member which presses the breast, and a transfer apparatus which moves the pressing member.

Typically, when the pressing member presses the breast, the patient feels pain and discomfort. Particularly, if an unexpected event such as power failure occurs, the pressing member may be stopped while the breast is being pressed by the pressing member. In this case, the patient will almost certainly experience a sense of fear or embarrassment. Therefore, when an unexpected event occurs, the pressing member must be able to release the breast.

Figure 1:
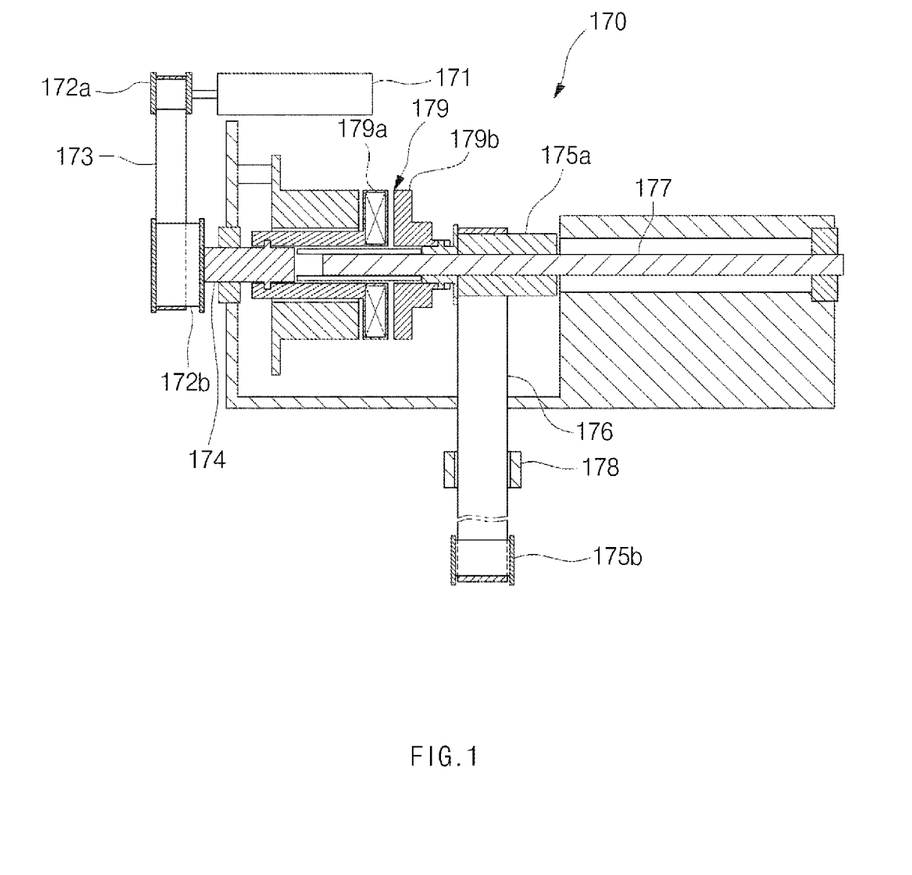
FIGS. 1 and 2 are sectional views of a transfer apparatus according to a conventional technique.

FIG. 1 is a sectional view illustrating a conventional transfer apparatus (at present, unpublished) for mammography machine which was proposed by the applicant of the present invention. This transfer apparatus is configured such that, upon power interruption, a breast pressing operation is automatically stopped so as to release the breast of a patient.

The transfer apparatus 170 of FIG. 1 includes a drive motor 171, a drive pulley 172a, a driven pulley 172b, a drive belt 173, a first drive shaft 174, a first pulley 175a, a second pulley 175b, a switch belt 176, a second drive shaft 177, a coupling member 178 and a clutch 179.

The first drive shaft 174 is interlocked with the drive pulley 172a, the driven pulley 172b and the drive belt 173.

The second drive shaft 177 is interlocked with the first pulley 175a, the second pulley 175b and the switch belt 176.

The coupling member 178 is coupled at a first side thereof to the switch belt 176. A second side of the coupling member 178 is coupled to a pressing member.

The clutch 179 has an effect of making the second drive shaft 177 dependent on the rotation of the first drive shaft 174. For this, the clutch 179 includes a first flange 179a which is interlocked with the first drive shaft 174, and a second flange 179b which is interlocked with the second drive shaft 177.

The first flange 179a generates magnetic force when power is supplied thereto. Thus, upon power being supplied, the second flange 179b is attached to the first flange 179a by the magnetic force of the first flange 179a. In this case, the second flange 179b can be rotated in conjunction with the rotation of the first flange 179a.

When the power is interrupted, the magnetic force of the first flange 179a is removed. Then, the second flange 179b is separated from the first flange 179a. As a result, the pressing member that has been pressing the breast of the patient automatically releases the breast.

Figure 2:
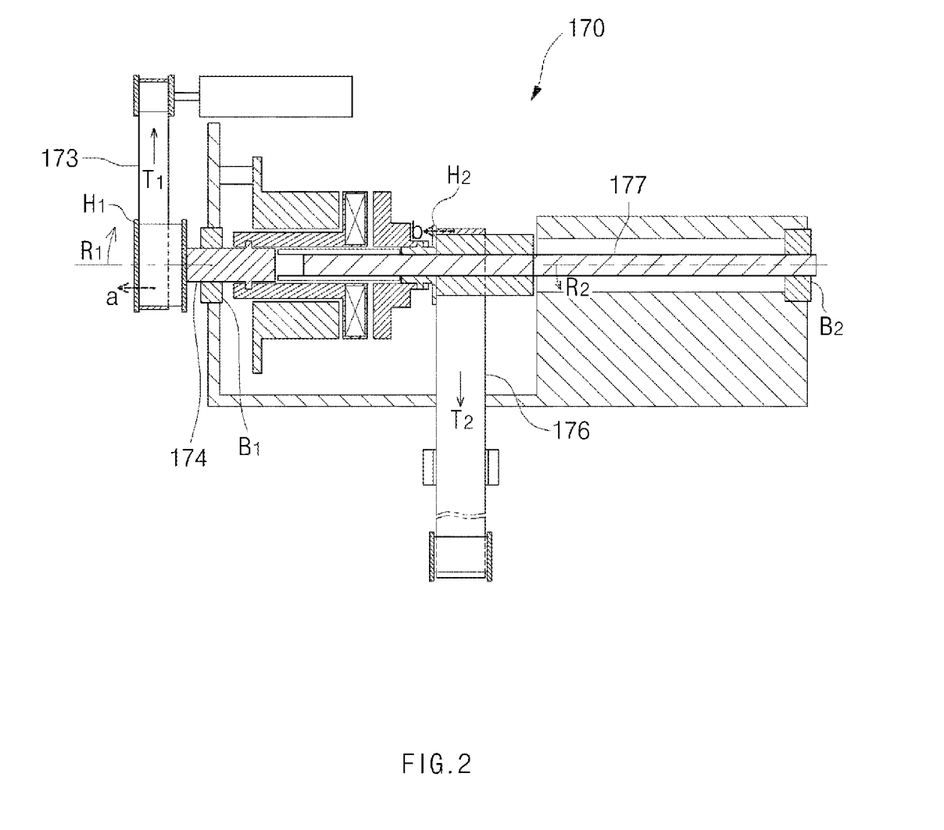

Meanwhile, as shown in FIG. 2, the tension T1 of the drive belt 173 and the tension T2 of the switch belt 176 respectively act as rotation momentum R1 to the first drive shaft 174 and as rotation momentum R2 to the second drive shaft 177. Thereby, the first drive shaft 174 rotates around a first bearing B1 within an allowance range (based on a tolerance or the like). The second drive shaft 177 rotates around a second bearing B2 within an allowance range (based on a tolerance or the like). Therefore, the rotating axes of the first drive shaft 174 and the second drive shaft 177 may be misaligned with each other rather than being parallel to each other. As a result, the drive belt 173 and the switch belt 176 may be biased to one side (refer to the arrows a and b of FIG. 2). If the drive belt 173 or the switch belt 176 that has been biased to one side makes contact with a flange portion H1 or H2 of the pulley 172b or 175a, noise is generated. Of course, the durability of the drive belt 173, the switch belt 176 and other elements may also be reduced.

DISCLOSURE OF THE INVENTION

Technical Problem

Accordingly, the present invention has been made keeping in mind the above problems occurring in the prior art, and an object of the present invention is to provide an X-ray photography machine which, despite using only a single drive shaft, is configured such that when supply of power is interrupted, a target that has been in a pressed state can be released.

Technical Solution

In order to accomplish the above object, the present invention provides an X-ray photography machine, including: a generator emitting an X-ray onto a target; a detector sensing the X-ray that has penetrated the target; a pressing member disposed between the generator and the detector; and a transfer apparatus moving the pressing member towards or away from the detector, the transfer apparatus having a drive source for providing a rotational force, a drive shaft rotated by the rotational force, a first flange fitted on the drive shaft, a second flange provided around the drive shaft with a space defined therebetween, the second flange being selectively coupled to the first flange, and a switch belt connected to the second flange, with the pressing member fastened to the switch belt.

Wherein either the first flange or the second flange selectively generates a magnetic force depending on supply of power, and a remaining one of the first flange and the second flange is magnetically coupled to the either the first flange or the second flange.

The X-ray photography machine further includes a first pulley provided around the drive shaft with a space defined therebetween, the first pulley being coupled to the second flange, wherein the switch belt is connected to the first pulley.

The X-ray photography machine further includes a second pulley spaced apart from a first pulley by a predetermined distance with respect to a direction in which the pressing member moves, wherein the switch belt connects the first pulley to the second pulley.

The X-ray photography machine further includes a drive pulley connected to the drive source; a driven pulley coupled to the drive shaft; and a drive belt connecting the drive pulley to the driven pulley.

Advantageous Effects

As described above, in an X-ray photography machine according to the present invention, a drive belt or switch belt can be prevented from being biased to one side. Therefore, the present invention can minimize problems such as abnormal noise, thus enhancing the reliability of the product.

BRIEF DESCRIPTION OF THE DRAWINGS

The above and other objects, features and advantages of the present invention will be more clearly understood from the following detailed description taken in conjunction with the accompanying drawings, in which.

MODE FOR CARRYING OUT THE INVENTION

Hereinafter, a preferred embodiment of the present invention will be described in detail with reference to the attached drawings.

For the sake of brevity, some explanation will be omitted or condensed if it is overlapping explanation or is not related to the characteristics of the present invention.

Figure 3:
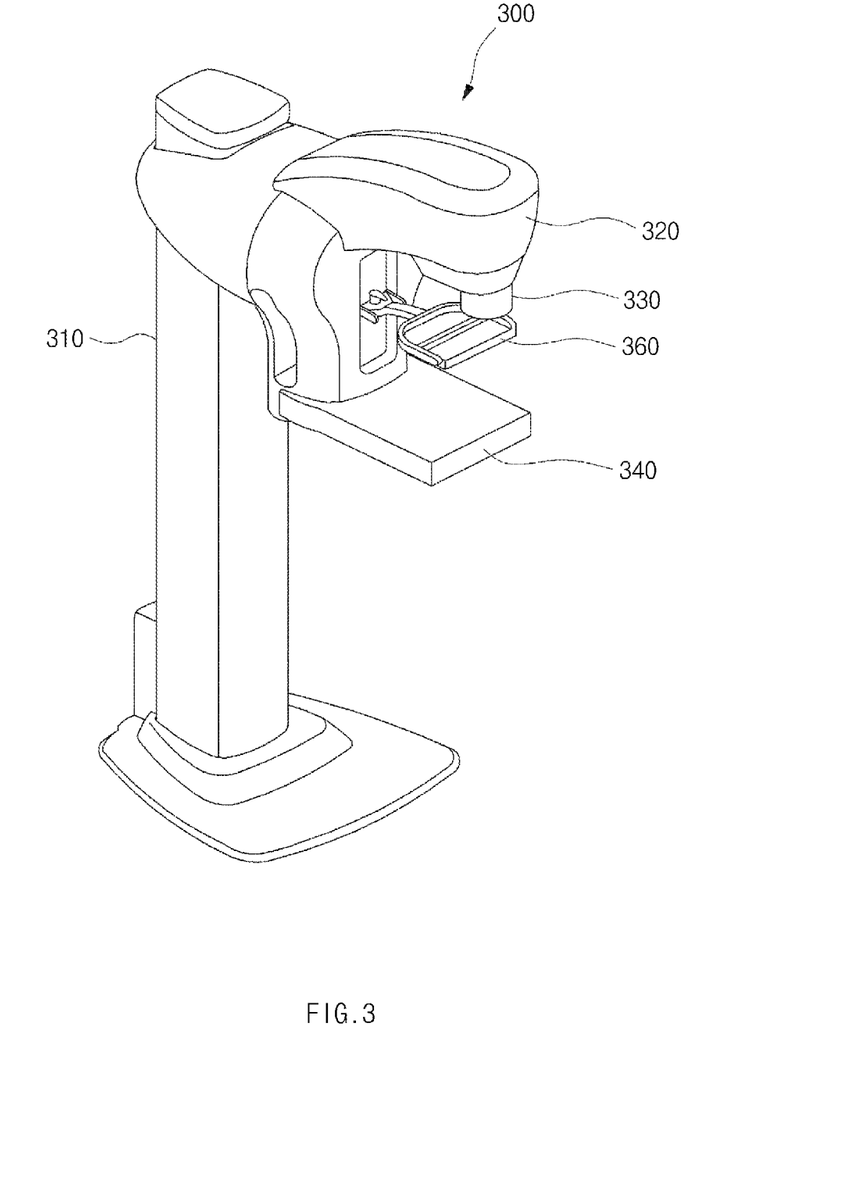
FIGS. 3 and 4 are perspective views illustrating a mammography machine, according to an embodiment of the present invention.

FIG. 3 is a perspective view of a mammography machine 300 according to an embodiment of the present invention.

Figure 4:
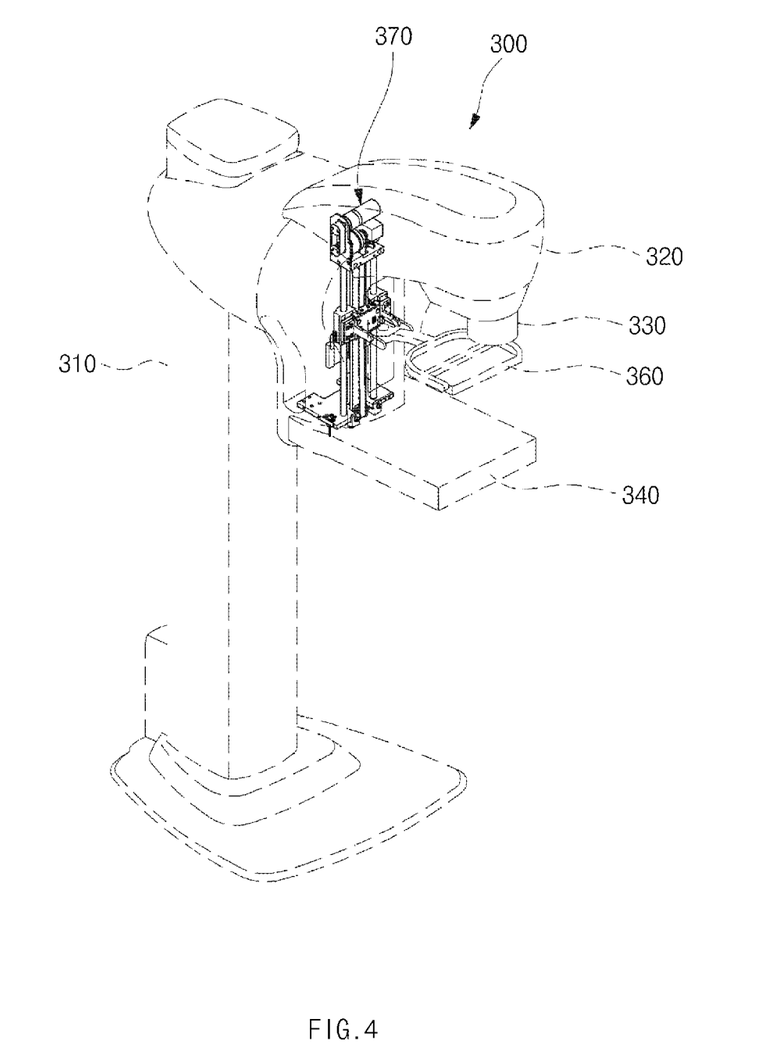

The mammography machine 300 includes a column 310, a C-shaped arm 320, a generator 330, a detector 340, a pressing member 360 and a transfer apparatus (370, refer to FIG. 4).

The column 310 supports the C-shaped arm 320.

The generator 330, the detector 340, the pressing member 360 and the transfer apparatus 370 are installed in or on the C-shaped arm 320. The C-shaped arm 320 is supported by the column 310 so as to be rotatable or liftable.

The generator 330 emits X-rays towards the detector 340.

The detector 340 senses X-rays which penetrate the breast of a patient that is being examined.

Figure 5:
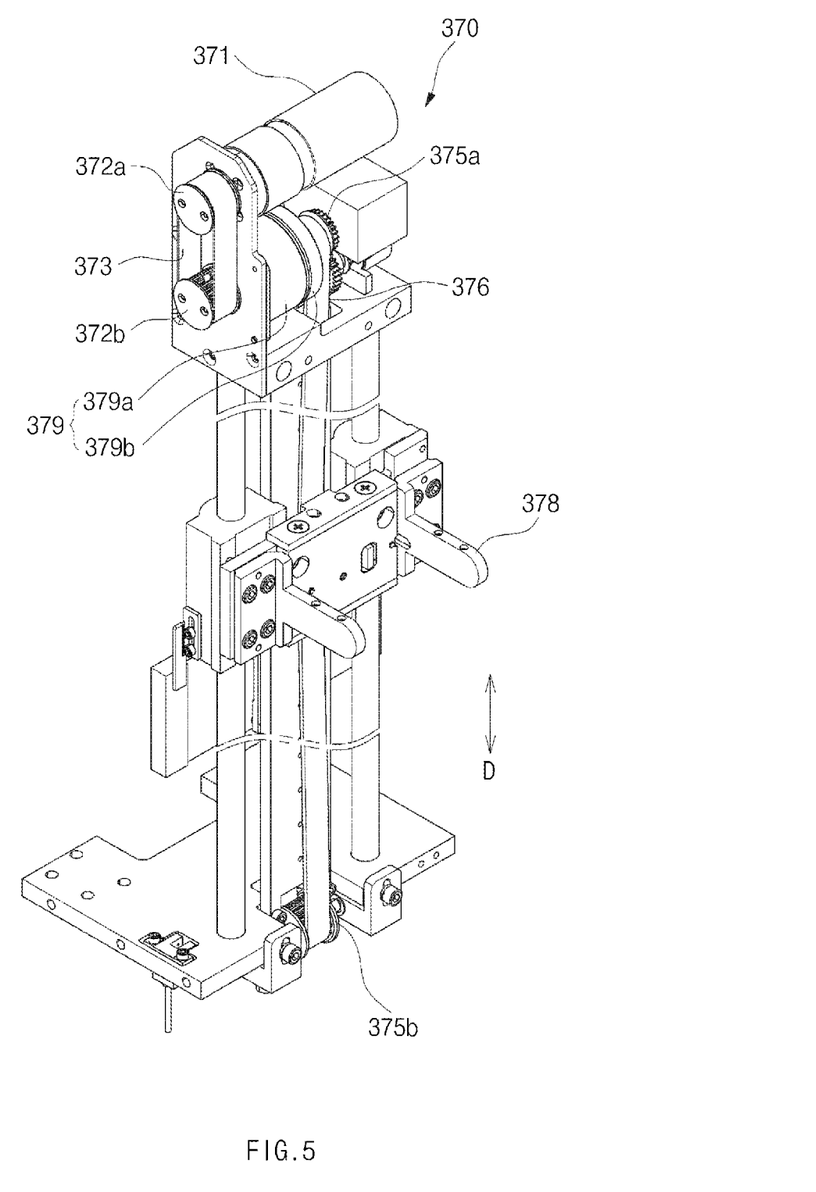
FIG. 5 is a perspective view of a transfer apparatus used in the mammography machine of FIG. 4.
Figure 6:
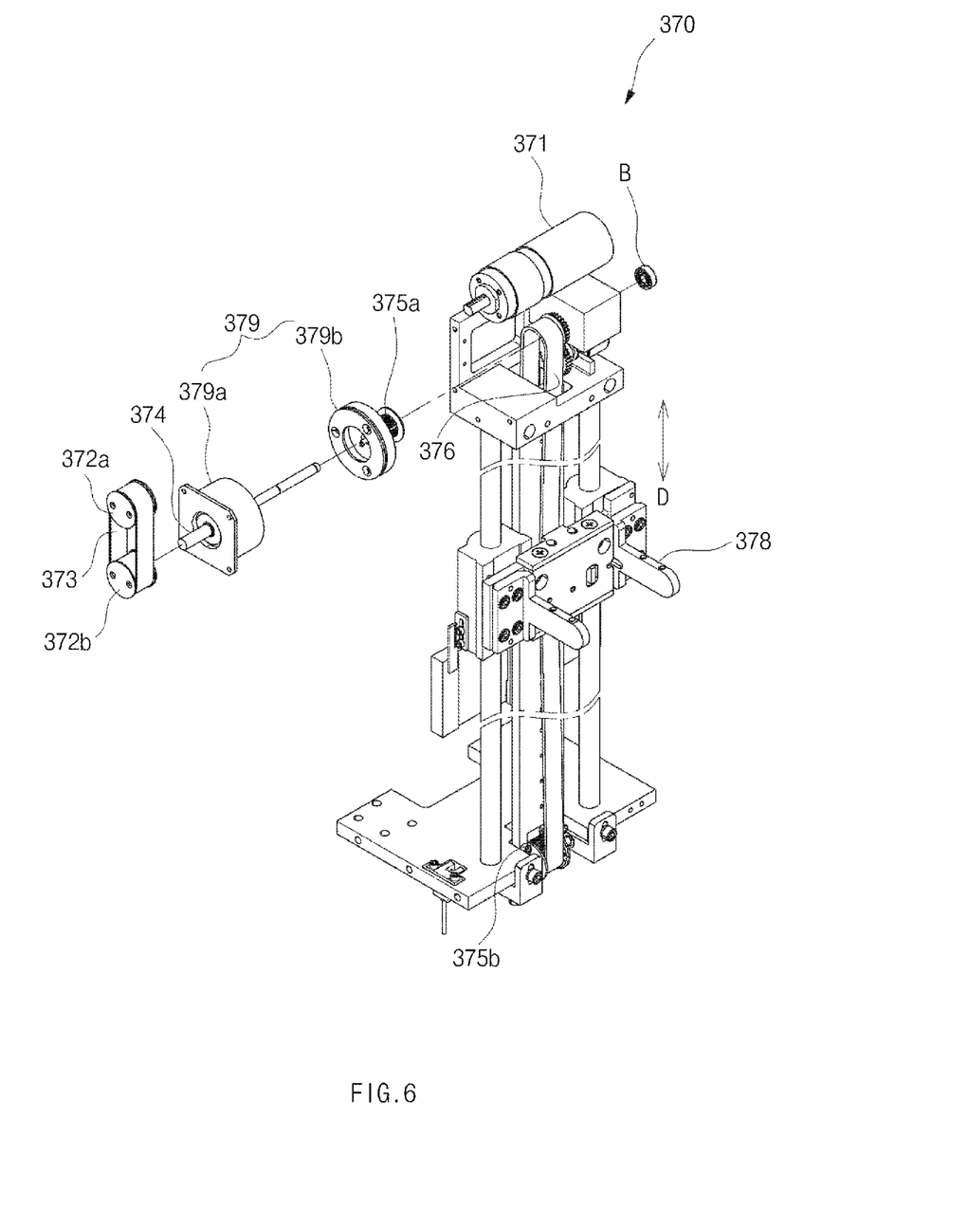
FIG. 6 is an exploded perspective view of a critical part of the transfer apparatus of FIG. 5.

The pressing member 360 is disposed between the generator 330 and the detector 340. The pressing member 360 linearly moves between the generator 330 and the detector 340 and presses the patient's breast that has been placed on the detector 340. As shown in FIG. 4, the transfer apparatus 370 is installed in an internal space of the C-shaped arm 320. The transfer apparatus 370 moves the pressing member 360. FIG. 5 is a perspective view of the transfer apparatus 370. FIG. 6 is an exploded perspective view of a critical part of the transfer apparatus 370. The transfer apparatus 370 includes a drive motor 371, a drive pulley 372a, a driven pulley 372b, a drive belt 373, a drive shaft 374, a first pulley 375a, a second pulley 375b, a switch belt 376, a coupling member 378 and a clutch 379.

The drive motor 371 serves as a drive source which provides drive force for moving the pressing member 360.

The drive pulley 372a is rotated by the operation of the drive motor 371.

The driven pulley 372b is coupled to a first end of the drive shaft 374.

The drive belt 373 rotates around the drive pulley 372a and the driven pulley 372b which are turning points.

The first end of the drive shaft 374 is coupled to the driven pulley 372b, and a second end thereof is supported by a bearing B.

Therefore, when the drive motor 371 is operated, the drive pulley 372a, the driven pulley 372b and the drive shaft 374 are rotated in conjunction with each other.

The first pulley 375a is selectively interlocked with the drive shaft 374. In other words, the first pulley 375a may be interlocked with the drive shaft 372 and rotated along with it, or the first pulley 375a may be released from the drive shaft 372.

The second pulley 375b is disposed at a position spaced apart from the first pulley 375a by a predetermined distance with respect to a direction in which the pressing member 360 linearly moves.

The switch belt 376 rotates around the first pulley 375a and the second pulley 375b that function as turning points.

The first pulley 375a, the second pulley 375b and the switch belt 376 are parts which convert the rotation of the drive shaft 374 into a linear motion of the pressing member 360.

The coupling member 378 is coupled at a first side thereof to the switch belt 376. A second side of the coupling member 378 is coupled to the pressing member 360. Therefore, when the switch belt 376 is rotated, the coupling member 378 and the pressing member 360 move linearly.

The clutch 379 has an effect of making the first pulley 375a selectively dependent on the rotation of the drive shaft 374.

For this, the clutch 379 includes a first flange 379a and a second flange 379b.

The first flange 379a is coupled to the drive shaft 374 and rotated along with the drive shaft 374. The first flange 379a comprises an electromagnet which generates magnetic force when power is supplied thereto.

The second flange 379b is coupled to the first flange 379a by magnetic force. The second flange 379b is coupled to the first pulley 375a. Therefore, when the first flange 379a is magnetically coupled to the second flange 379b, the first pulley 375a becomes dependent on the rotation of the drive shaft 374.

Of course, it is also preferable that the second flange 379b comprise an electromagnet, when necessary.

Figure 7:
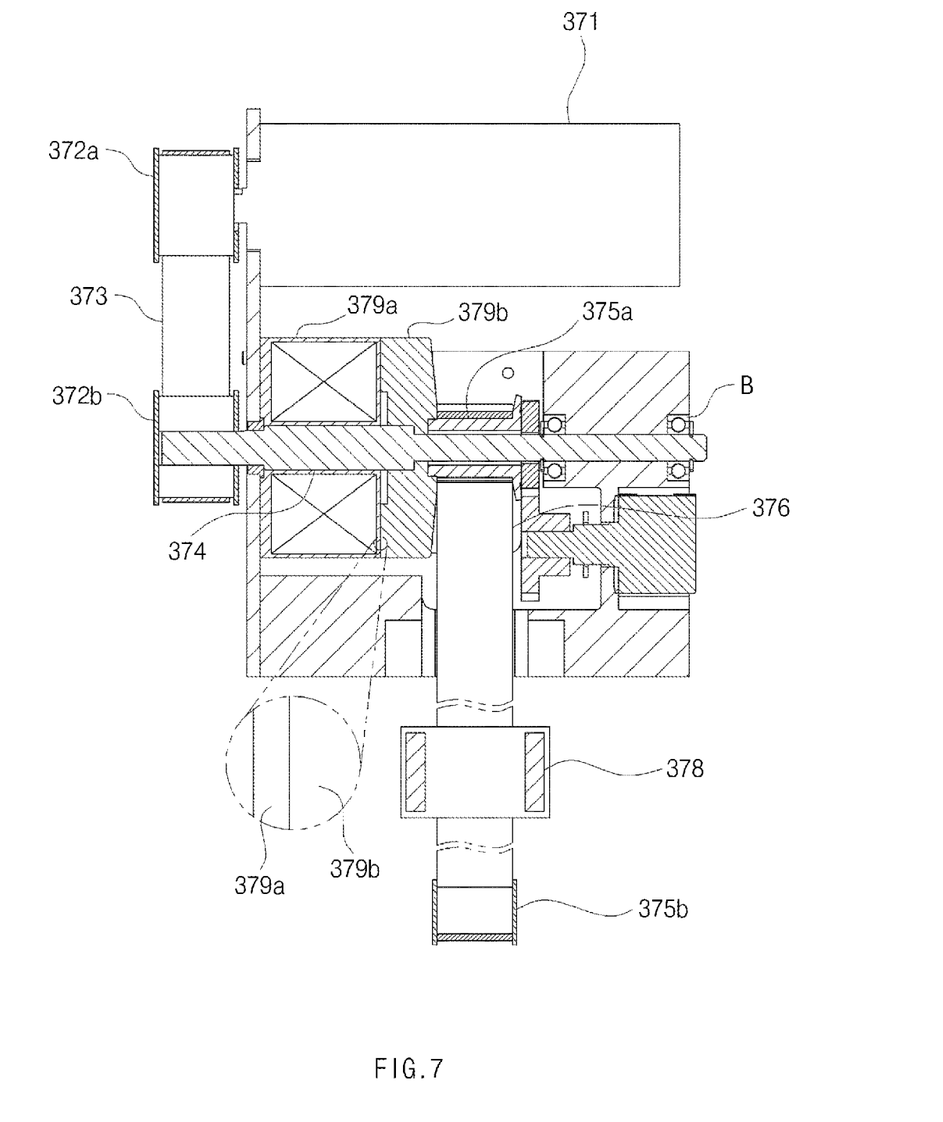
FIGS. 7 and 8 are sectional views of the critical part of the transfer apparatus of FIG. 5.

FIG. 7 is a sectional view showing the second flange 379b that has been magnetically coupled to the first flange 379a.

In the state of FIG. 7, the drive force of the drive motor 371 is transmitted to the pressing member 360 via the drive pulley 372a, the drive belt 373, the driven pulley 372b, the drive shaft 374, the first flange 379a, the second flange 379b, the first pulley 375a, the switch belt 376 and the coupling member 378, successively. Depending on whether the drive motor 371 rotates in the normal direction or rotates reversely, the pressing member 360 linearly moves between the generator 330 and the detector 340 upwards or downwards.

If the supply of power to the first flange 379a is interrupted by manipulation of an operator or an unexpected event such as power failure, the magnetic force of the first flange 379a is removed. Eventually, as shown in an enlarged view of FIG. 8, the second flange 379b is separated from the first flange 379a.

Figure 8:
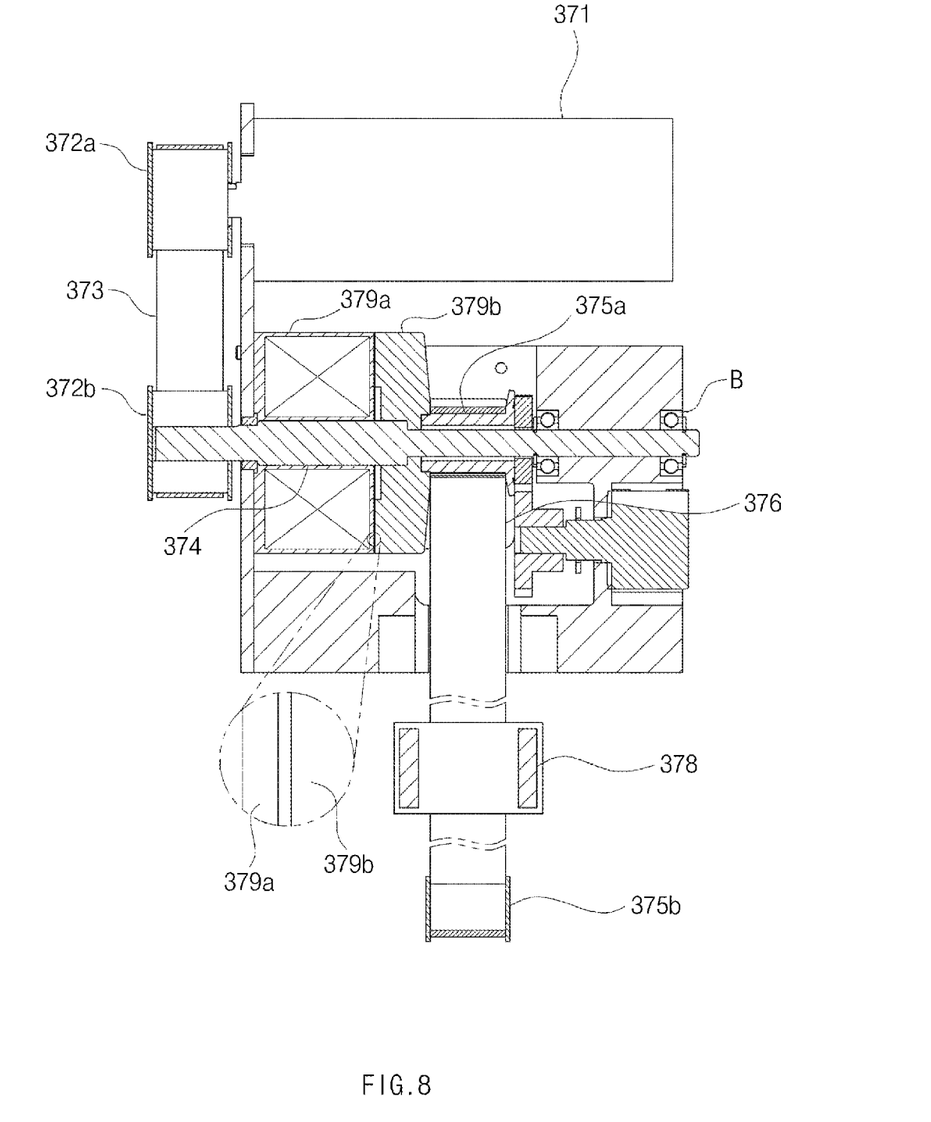

In the state of FIG. 8, the first pulley 375a is released from the drive shaft 374. Thereby, the pressing member 360 that has been pressing the breast of the patient releases the breast. For this, a first portion of the drive shaft 374 is fixed to the first flange 379a, while a second portion thereof passes through the second flange 379b and first pulley 375a with a predetermined space defined therebetween. The end of the second portion of the drive shaft 374 is supported by the bearing B.

Meanwhile, the reason that magnetic force is used to couple the first flange 379a to the second flange 379b is because excessive pressure must not be applied to the breast of the patient.

Furthermore, in the above-mentioned embodiment, although the detector 340 has been illustrated as supporting the breast of the patient, a separate support may be used to support the breast.

Preferably, timing belts are used as the drive belt 373 and the switch belt 376 to enhance the precision of transmission of power. Also, timing pulleys are preferably used as the drive pulley 372a, the driven pulley 372b, the first pulley 375a and the second pulley 375b.

Although the preferred embodiment of the present invention has been disclosed for illustrative purposes, those skilled in the art will appreciate that various modifications, additions and substitutions are possible, without departing from the scope and spirit of the invention as disclosed in the accompanying claims.

The invention claimed is:

1. An X-ray photography machine, comprising:
   a generator emitting an X-ray onto a target;
   a detector sensing the X-ray that has penetrated the target;
   a pressing member disposed between the generator and the detector; and
   a transfer apparatus moving the pressing member towards or away from the detector,
   wherein the transfer apparatus includes a drive source for providing a rotational force;
   a drive shaft rotated by the rotational force;
   a first flange fitted on the drive shaft;
   a second flange provided around the drive shaft with a space defined therebetween, the second flange being selectively coupled to the first flange; and
   a switch belt connected to the second flange, with the pressing member fastened to the switch belt.

2. The X-ray photography machine as set forth in claim 1, wherein either the first flange or the second flange selectively generates a magnetic force depending on supply of power, and a remaining one of the first flange and the second flange is magnetically coupled to the either the first flange or the second flange.

3. The X-ray photography machine as set forth in claim 1, further comprising a first pulley provided around the drive shaft with a space defined therebetween, the first pulley being coupled to the second flange, wherein the switch belt is connected to the first pulley.

4. The X-ray photography machine as set forth in claim 3, further comprising:
   a second pulley spaced apart from a first pulley by a predetermined distance with respect to a direction in which the pressing member moves, wherein the switch belt connects the first pulley to the second pulley.

5. The X-ray photography machine as set forth in claim 3, further comprising:
   a drive pulley connected to the drive source;
   a driven pulley coupled to the drive shaft; and
   a drive belt connecting the drive pulley to the driven pulley.

* * * * *